(12) United States Patent
Stroganov et al.

(10) Patent No.: US 9,389,168 B2
(45) Date of Patent: Jul. 12, 2016

(54) MERCURY MONITOR

(71) Applicants:Alexander Anatolyevich Stroganov, St. Petersburg (RU); Sergey Evgenievich Sholupov, St. Petersburg (RU); Pavel Vladimirovich Pitirimov, St. Petersburg (RU)

(72) Inventors: Alexander Anatolyevich Stroganov, St. Petersburg (RU); Sergey Evgenievich Sholupov, St. Petersburg (RU); Pavel Vladimirovich Pitirimov, St. Petersburg (RU)

( * ) Notice: Subject to any disclaimer, the term of this patent is extended or adjusted under 35 U.S.C. 154(b) by 0 days.

(21) Appl. No.: 14/768,142

(22) PCT Filed: Jan. 20, 2014

(86) PCT No.: PCT/RU2014/000031
§ 371 (c)(1),
(2) Date: Sep. 17, 2015

(87) PCT Pub. No.: WO2014/126507
PCT Pub. Date: Aug. 21, 2014

(65) Prior Publication Data
US 2016/0033391 A1   Feb. 4, 2016

(30) Foreign Application Priority Data
Feb. 15, 2013   (RU) ................. 2013107775

(51) Int. Cl.
*G01J 3/28* (2006.01)
*G01N 21/03* (2006.01)
*G01N 21/31* (2006.01)
*G01N 21/11* (2006.01)

(52) U.S. Cl.
CPC ............... *G01N 21/0332* (2013.01); *G01J 3/28* (2013.01); *G01N 21/11* (2013.01); *G01N 21/3103* (2013.01)

(58) Field of Classification Search
CPC . G01N 21/11; G01N 21/0332; G01N 21/255; G01J 3/42; G01J 3/08; G01J 1/36; G01J 1/16; G01J 3/28
See application file for complete search history.

(56) References Cited

U.S. PATENT DOCUMENTS

| 5,679,957 A | 10/1997 | Durham et al. |
| 5,939,648 A | 8/1999 | Phan |
| 2006/0245973 A1* | 11/2006 | Kita ................... G01N 33/0013 422/68.1 |

FOREIGN PATENT DOCUMENTS

RU   2110060 C1   4/1998

OTHER PUBLICATIONS

International Search Report for App. No. PCT/RU2014/000031 mailed May 29, 2014.

* cited by examiner

*Primary Examiner* — Abdullahi Nur
(74) *Attorney, Agent, or Firm* — Walker & Jocke (57) ABSTRACT

An exemplary embodiment provides an analytical system for measurement of mercury concentration that can be used to monitor mercury concentration in industrial and sewage water and combustion gases.

16 Claims, 5 Drawing Sheets

MERCURY MONITOR

TECHNICAL FIELD

An exemplary embodiment includes an analytical system for automatic measurement of mercury concentration in sample material. Exemplary embodiments can be used to monitor mercury concentration in industrial and sewage water and combustion gases.

BACKGROUND

Measurement of mercury concentration is needed for many quality control processes. Mercury is a common toxin located in many places from many sources.

A mercury analyzer known as a PA-2 Mercury Process Analyzer produced by Mercury Instruments of Germany was designed for continuous measurement of the concentration of mercury in industrial sewage water used by enterprises dedicated to burning of waste, thermal power plants, treatment facilities, etc. The mercury monitor contains: a sample preparation module where the preliminary oxidation of a sample with corresponding reagent takes place, a reduction module where mercury is reduced to an atomic state upon addition of a reducer; a gas exchange unit where elemental mercury is released from the liquid sample and comes into a carrier gas, and an analytical cell where the carrier gas delivers elemental mercury and where the amount of released mercury is determined via the atomic absorption method.

U.S. Pat. No. 5,679,957 discloses a device to monitor mercury emissions containing an input unit for a gas sample to be analyzed, a thermal atomizer where all mercury compounds dissociate to provide formation of elemental mercury, an analytical cell capable of being heated that considerably decreases the rate of oxidation of elemental mercury with dissociation products and matrix components. An atomic absorption spectrometer measures elemental mercury.

A mercury monitor of combustion gases known as an MERCEM300Z Mercury Analyzer produced by the firm Sick of Germany, consists of a sampling probe, a gas line, a sample input unit, a thermal atomizer, a analytical cell capable of being heated, a atomic absorption spectrometer and a return pump. Combustion gas is taken with a sampling probe and is transported to the input part of the monitor. Gas passes into a thermal atomizer where all mercury, irrespective of its form, in combustion gas is transformed into elemental form, and comes to an analytical cell where mercury concentration is determined by an atomic absorption spectrometer. A return pump is attached to the analytical cell exit. The thermal atomizer and the analytical cell temperature is 1000° C.

Such prior systems contain various limitations that an exemplary embodiment seeks to solve.

SUMMARY

Pollution in the form of material accumulation on the windows of an analytical cell leads to considerable decrease in transparency and intensity of the probing radiation output by a atomic absorption spectrometer through the sample material. As a result, deterioration of analytical characteristics and even the impossibility to carry out measurements may occur. Therefore, it is impossible to use this configuration to determine the content of mercury in sample materials comprising industrial waters of various enterprises such as when water contains high percentage concentrations of chlorides and sulfates of metals (hardness salts). This is because evaporation and atomization of such materials lead to formation of vapors of these salts which precipitate on the analytical cell windows. Additionally, monitors with such analytical cells may only have a short period of unattended operation, because of pollution of the analytical cell windows. Eventually because of precipitation of high concentration dissolved salts, the walls of the input sample unit and the thermal atomizer get blocked gas channels which makes the device unusable.

An exemplary embodiment of the mercury monitor apparatus is an improvement with improved characteristics, such as an increase in unattended operating time of an analytical cell and associated monitor system, and an extended functioning life of the monitor.

DETAILED DESCRIPTION

An exemplary embodiment of the mercury monitor includes a input sample unit, a thermal atomizer, an analytical cell capable of being heated, a gas collector unit, and a return pump. The analytical cell contains two windows that are generally transparent windows for resonant radiation of mercury, at least one of which is optically coupled with an atomic absorption spectrometer. At least one gas sample inlet port serves as a input gas port and is located in the central part of the body of the analytical cell used in conjunction with the atomic absorption spectrometer. The analytical cell includes at least two gas outlet ports, each of which is located longitudinally intermediate between the input gas port and the corresponding adjacent window. A sample input unit is coupled with an injecting pump capable of introducing the sample material to be analyzed into the thermal atomizer. The exemplary analytical cell has clean gas inlet flow ports or openings located in the body adjacent its both ends. This provides a flow of sample vapor free gas between the adjacent window and the nearest output gas port.

An exemplary embodiment provides a protective air stream between each window of analytical cell and the sample gas to be analyzed, preventing direct contact between the hot gas to be analyzed arriving in the analytical cell and the cold surface of each window. Therefore, vapors of highly volatile compounds present in the sample gas to be analyzed are not condensed on the windows of the analytical cell, and the transmission coefficient of the windows for the probing radiation of the atomic absorption analyzer remains sufficiently transparent in the working range for a long time.

An exemplary embodiment of the mercury monitor also contains a nebulizer. A nebulizer holder internal wall and the nebulizer bound a cavity. The cavity is connected with an internal cavity of a thermal atomizer. The holder contains a port connecting the cavity with a carrier gas supply. The nebulizer includes a spraying nozzle, a liquid input port and a gas input port which is operatively connected by gas-liquid communication with the carrier gas supply. The carrier gas supply input port of the nebulizer is connected to a mixer with three ports; the one port is connected to the carrier gas source, the second port is connected to a water supply, and another port of the mixer is connected to the gas input port of the nebulizer.

A gas collector unit is operatively connected with the gas outlet ports of the analytical cell. The gas collector includes a vapor gas conduit, a gas-liquid separator and a liquid collection reservoir.

The exemplary analytical cell is optically connected with the spectrometer through a first window, and with a retroreflector through a second window. The retroreflector is aligned such that the probing radiation beams of the spectrometer having passed through the first window and through the second window, return back through the second window to the sensing element of the spectrometer through the first window.

Use of the nebulizer in an exemplary embodiment of the mercury monitor enables elimination of a mechanical water sample supply to the atomizer. This allows for increased reliability of the supplying device, as well as the ability to input a sample in the form of an aerosol which reduces amount of salts precipitating on the atomizer wall. Water supplied into the nebulizer compressed air carrier gas in the cavity provides a decreased amount of the salts precipitating directly in nozzle of the nebulizer. Use of the gas-liquid separator for treating the vapor gas after leaving the analytical cell enables removal of water vapor from output gas stream. This eliminates condensation of water in the return pump and enables the pump to work in its regular operating mode. Use of the exemplary optical scheme at which radiation beams from the atomic absorption spectrometer passing through the analytical cell comes to a retroreflector, returns into the analytical cell and then goes to a photo detector, doubles the sensitivity of the analysis for the same linear size of analytical cell. Additionally, the exemplary embodiment provides compactness of spectrometer construction that increases stability of work of the entire spectrometer.

Figure 1:
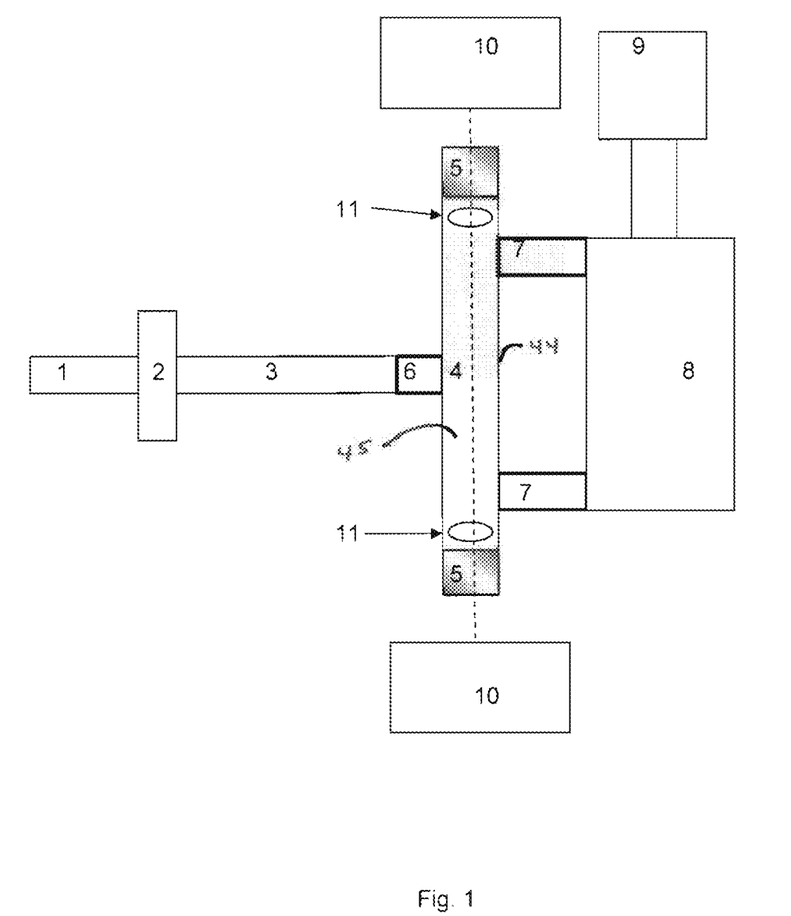
FIG. 1 shows a schematic representation of an exemplary mercury monitor system.

An exemplary embodiment of the mercury monitor represented in FIG. 1, contains an injecting pump 1, a sample input 2, a thermal atomizer 3, an analytical cell 4 with windows 5. The analytical cell includes gas sample inlet port 6 and gas outlet ports 7. The monitor further includes the gas collector 8, the return pump 9, and also the atomic absorption spectrometer 10. The analytical cell has clean gas inlet flow ports comprising openings 11 that introduce sample vapor free gas into the cell longitudinally between windows 5 and the outlet ports 7.

Figure 2:
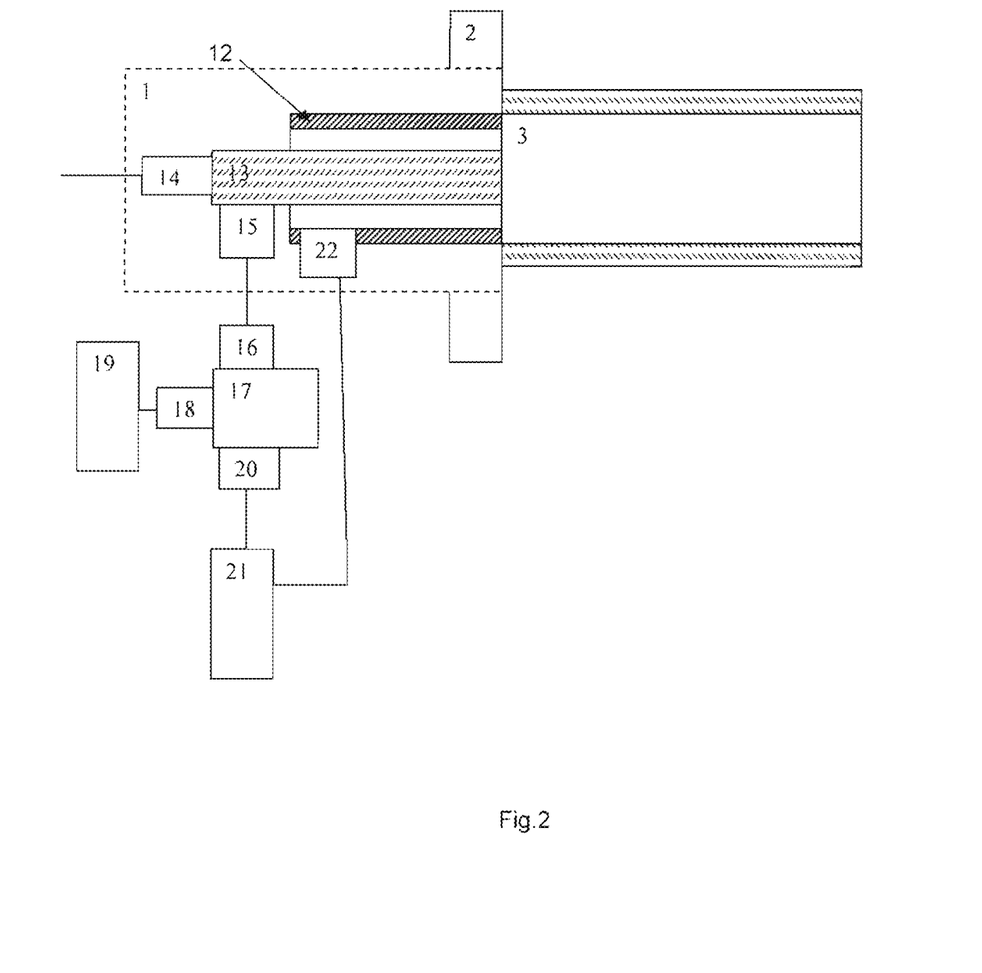
FIG. 2 shows a schematic representation of an input unit with a nebulizer and a gas supply means.

An exemplary embodiment includes an injecting pump 1 is shown in FIG. 2. The nebulizer 13 is positioned in a nebulizer holder 12 in such a way that its nozzle is directed towards an internal part of a thermal atomizer 3. The nebulizer assembly is positioned in the sample input unit 2. The liquid port 14 of the nebulizer 13 is fluidly connected to a switching liquid tap (not shown), which alternatively connects the port 14 of the nebulizer with reservoirs containing distilled water, standard solution, and the sample material to be analyzed. The gas port 15 of the nebulizer 13 is connected to a first port 16 of a mixer 17, whose second port 18 is connected to a water supply 19, and its third port 20 is connected to a carrier gas supply 21. The carrier gas supply is also connected to the cavity that extends between the nebulizer 13 and its holder 12, through the holder port 22.

In an exemplary embodiment, when determining the concentration of mercury in combustion gases, the unit of the injecting pump 1 may include a diaphragm pump that operates to supply gas to be analyzed from the sampling line (not shown) directly to the interior area of the thermal atomizer 3.

In an exemplary embodiment the thermal atomizer 3 can include a quartz tube whose one end is hermetically fluidly connected to sample input unit 2, and the second end is hermetically fluidly connected to the gas sample inlet port 6 of the analytical cell 4. The quartz tube is positioned coaxially with the nebulizer 13 and its holder 12, such that the internal diameter of the quartz tube is no less than the internal diameter of the nebulizer holder 12. The heater controller of an exemplary arrangement operates to maintain temperature inside the quartz tube in the range of 600-700° C. The entire thermal atomizer assembly is placed into a metal protection enclosure.

The exemplary analytical cell 4 is made in the form of a cylindrical body 44 that generally bounds an interior area 45. The body extends along a longitudinal direction. A gas sample inlet port 6 is hermetically welded to the middle part of the body and two framed windows 5 are installed adjacent the opposed longitudinal body ends. The gas outlet ports 7 are positioned longitudinally between the windows 5 and the inlet port 6 on each respective side of the inlet port. In order to form a protective air stream, the clean gas inlet flow ports or openings 11 provide additional inlet ports through which clean gas not containing sample vapor in the form of air, can come into the interior area of the analytical cell longitudinally between the windows 5 and the gas output ports 7. This clean gas flow helps to reduce the accumulation of material on the windows. Heaters maintaining temperature of the gas to be analyzed in the range of 600-750° C. are positioned in the interior area of the cell.

Figure 3:
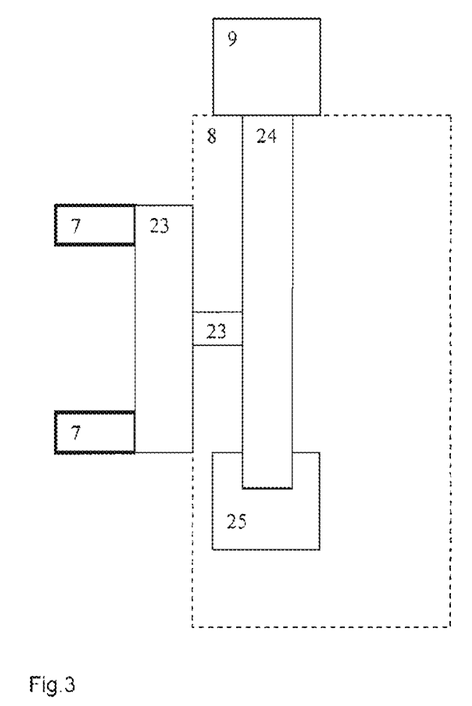
FIG. 3 shows a schematic representation of the gas collector unit.
Figure 4:
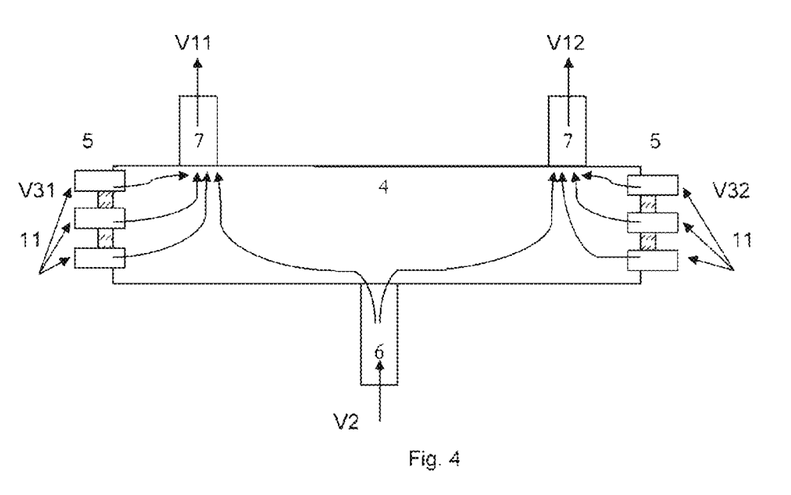
FIG. 4 shows a gas flow scheme for achieving protection of analytical cell windows from material accumulation.
Figure 5:
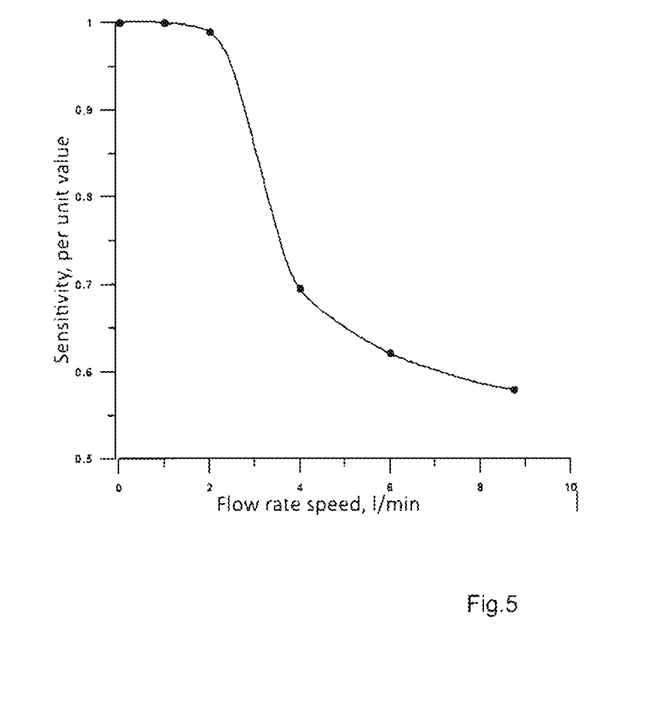
FIG. 5 shows a graph of sensitivity dependence on flow rate of a sucking out pump.

In an exemplary embodiment the gas collector 8 receives the gas from the gas outlet ports 7 of the analytical cell 4. The analytical cell outlets are operatively connected through vapor-gas conduits 23 to the gas-liquid separator 24. The separator can be in the form of a return gas cooler or refrigerator in whose external condenser jacket cooling water flows, and the steam-gas mixture comes into its internal part. One end of the separator 24 is operatively connected to a liquid collection reservoir 25 where water is collected after cooling of the vapor-gas mixture. The separator 24 is connected to a return pump 9, which in the exemplary embodiment includes a diaphragm pump.

The atomic absorption spectrometer 10 can be used as the atomic absorption analyzer of mercury concentration utilizing the direct Zeeman effect which is characterized by high selectivity of measurements. The Zeeman effect is described in a publication of A. A. Ganeev, et al., herein incorporated by reference. (A. A. Ganeev, S. E. Shopulov, M. N. Slyadnev, *Zeeman modulation polarization spectrometry as variance of atomic—absorption analysis: possibilities and constraints*, JAC, 1996, v. 51, no. 8, p. 855-864) which is incorporated herein by reference in its entirety.

Figure 6:
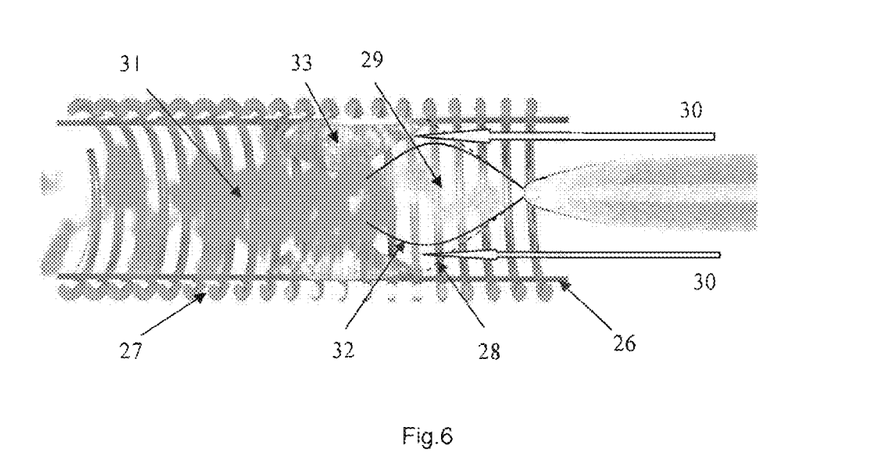
FIG. 6 shows a graphic representation of a model for spraying water aerosol in a thermal atomizer.
Figure 7A:
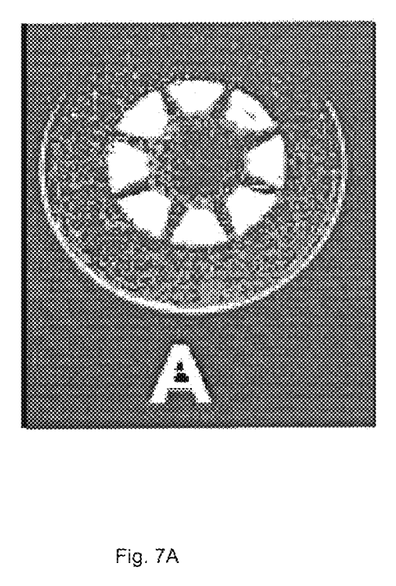
FIG. 7A shows a window of the analytical cell with protective air stream after 14 days of operation.
Figure 7B:
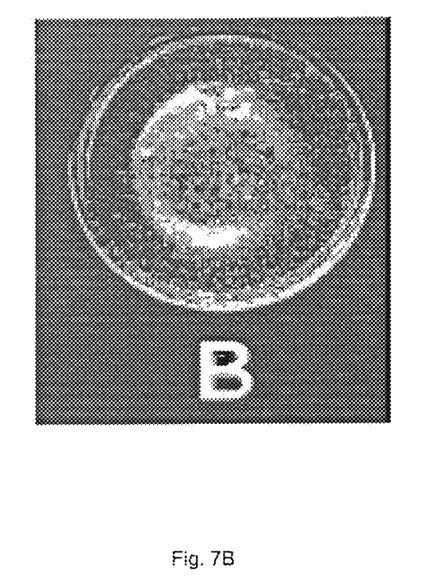
FIG. 7B shows a window of an analytical cell after 8 hours without a protective air stream.

Upon injection of water aerosol into the thermal atomizer, as represented in FIG. 6, part of the aerosol evaporates directly in the carrier-gas, and a part 28 (without full evaporation of water) reaches the heated walls of the atomizer—the quartz tube 26 placed in the heater 27 which part 28 is determined by water aerosol spraying at a finite angle 29. In order to increase the time spent by water aerosol in the carrier gas, in the exemplary arrangement an air stream 30 is additionally injected between the nebulizer and its holder.

Furthermore, this additional air stream 30 extends along walls of the thermal atomizer and thereby helps to retain the main stream of aerosol in an axial zone of the atomizer interior where evaporation of water from an aerosol particle along with formation of salt aerosol 31 takes place. An increase in water aerosol 32 motion trajectory leads to an increase of evaporated water aerosol in carrier gas, and a decrease in precipitation rate of salt 33 on the wall of the thermal atomizer. This results in an increase in operating life of the unattended thermal atomizer.

During transportation of the salt aerosol inside the thermal atomizer and in the heated analytical cell (the exemplary analytical cell temperature is 650-750° C.) salt compounds partially evaporate from the aerosol particle surface and pass into carrier-gas in the form of vapor. Similarly, the salt compounds that are precipitated on the atomizer surface, when heated, partially evaporate and pass into the carrier gas. Finally, the interaction of salt particles with the surface of the heaters of the analytical cell partially evaporates such particles, and the vapors pass into the carrier gas.

To reduce the radiation beam blocking effect from precipitation of vapors of highly volatile compounds in sample vapor from carrier gas on the surfaces of the windows of the analytical cell, an exemplary embodiment of the mercury monitor was designed to have windows maintained in and blown with clean air, and having no direct contact between the cell windows with the sample containing carrier gas. The protection scheme for the exemplary analytical cell windows is represented in FIG. 4. Gas is pumped out from the analytical cell through the outlet ports 7 with volume speed V1=V11+V12. The gas analyzed is supplied through the inlet port 6 with volume speed V2. The return pump 9 creates negative pressure evacuation in the outlet ports 7 and, in the analytical cell, the cell pressure is lower than atmospheric, respectively. Ambient air stream flow from the inlet flow ports 11 in the analytical cell is created due to evacuation in the analytical cell. As openings 11 are located in immediate outboard longitudinal proximity to the outlet ports, the created air stream enters openings 11 and generally immediately leaves the interior area through the outlet ports 7, without extending along a longitudinal axis of the analytical cell.

The volume speed of the return pump V1 is higher than volume supply speed of gas analyzed in the analytical cell V2, therefore, the volume speed of protective air stream V3=V31+V32 will make the value V3=V1−V2. Dependence of measurement sensitivity on speed of the return pump V1 at constant rate of supply of gas vapor analyzed V2=2 l/min is shown in FIG. 5. If pumping out speed is less than supply speed (0-2 l/min), the gas analyzed occupies the entire cell, including the regions between the outlet ports 7 and cell windows 5, sensitivity being maximized (under existing experiment conditions, sensitivity is proportional to the effective length of the analyzed gas layer).

With an increase in pumping out speed (2-4 l/min) the gas analyzed from the regions between windows 5 and the outlet ports 7 are replaced with atmospheric air, and consequently the sensitivity of measurements drops. The further increase in pumping-out speed (4-9 l/min) leads to negligible change of sensitivity, i.e. increase of pumping speed leads only to increase in protective air stream with only an insignificant decrease of effective length of the layer of the gas analyzed.

The concentration of mercury in the air must be such that the air which entered into the analytical cell (together with mercury) should not effect results of mercury measurement in a water sample. In an exemplary embodiment, concentration of mercury should not exceed a value of 6 $\mu g/m^3$ (at 1 hour stability at the level of 10%) that is virtually equal to threshold allowable concentration in working area (10 $\mu g/m^3$).

The output of a pressure pump is connected to the sample input unit 2 after which gas analyzed comes into the thermal atomizer 3 whose temperature is 800-950° C.

This temperature is enough to convert fixed mercury to elemental form, and also to considerably decrease the rate of oxidation of elemental mercury. Gas from the thermal atomizer is transported in the analytical cell 4 heated to 850-950° C., through its sample inlet port. In an exemplary embodiment, to protect the windows against precipitation of volatile compounds which are present in the gas being analyzed, the analytical cell has a construction at which windows are blown with clean air that prevents direct contact of the window with gas analyzed. In an exemplary embodiment, the gas outlet of the analytical cell is connected to the gas collector unit in which temperature of gas that has been analyzed decreases to a level, which allows return pumping to be performed. As the return pump provides a higher flow than the pressure pump delivering gas to the inlet port, it leads to creation of a differential pressure air stream through clean gas inlet port openings about the inside of the windows of the analytical cell, thereby protecting the windows from pollution.

In an exemplary embodiment, the mercury monitor enables increasing the interval of unattended operation by at least by 40 times.

EXAMPLES

Exemplary embodiments of a mercury monitor using the principals described herein are further illustrated by the following examples, which are set forth to illustrate the presently disclosed subject matter and are not to be construed as limiting.

Example 1

Determination of Total Content of Mercury in Technological Water of a Thermal Power Plant Technological water contains a high concentration of dissolved hardness salts (1-5%). The water to be analyzed comes into the tank which is connected to the input of the switching liquid tap. Other inputs of the valve are connected to the distilled water reservoir and with standard solution, necessary to carry out blank measurement and calibration of the atomic absorption spectroscopy monitor.

The output of the switching liquid tap is connected to the liquid port of the nebulizer. The source of compressed air is connected to the gas port of the nebulizer. Compressed air purified of dust and oil vapors, for example, by means of dust and an oil filter, passes through the nebulizer, creates evacuation in the region of the gas nozzle (Venturi's effect) that leads to suction of liquid from the liquid channel of the nebulizer and coming to the gas nozzle. Slowly incoming liquid is affected in the gas nozzle by the fast air stream that leads to formation of water aerosol which comes into the thermal atomizer.

In the exemplary thermal atomizer whose temperature is in the range of 600-700° C., water evaporates from aerosol particles and all mercury contained in them converts into atomic form at this temperature. Upon evaporation of water the small solid particles of salts (salt aerosol) are formed and are present in suspension in the air which serves as carrier gas. Further all formed components are transported by the carrier gas into the interior area of the analytical cell through its gas sample inlet port.

Simultaneously, the atmospheric air comes into the analytical cell through clean gas inlet flow port openings, preventing direct contact of the gas being analyzed with the surfaces of the windows. A steam-gas mixture comes out from the gas outlet ports of the analytical cell through the vapor gas conduit gas tee into the liquid gas separator, made as the return gas cooler in whose external cooling jacket the cooling water flows.

The second end of the vapor gas conduit gas tee is connected with a pipeline of the liquid gas separator to the liquid collection reservoir in which the water is condensed in the return cooler and is collected. The pipeline is installed in such a way that its second end in the liquid collection reservoir is always below water level (at the monitor start up, an additional amount of water is filled in this reservoir), thus, it performs the function of a water lock for the gas part. The second end of the return cooler or refrigerator is connected to the return pump, inducing the sucking-out of the gas stream after the analytical cell.

Upon formation of water aerosol inside of the nebulizer, the part of formed aerosol precipitates on the internal wall of the gas nozzle. As the water analyzed contains a high concentration of hardness salts, evaporation of water from precipitated aerosol leads to accumulation of salts on internal surface of the gas nozzle that causes a change of nozzle geometry and fast contamination of the nebulizer. In an exemplary arrangement to eliminate contamination of the nebulizer an additional amount of distilled water is introduced into the nebulizer cavity with compressed air and continuously washes out the nozzle and removes precipitated salts from it.

Example 2

Protective Air Stream Vs. Without Protective Air Stream

An exemplary embodiment of the analytical cell unit has been tested via analysis using a real water sample. FIG. 7A shows the windows with a protective air stream. FIG. 7B shows the windows without the protective air stream. The Figures allows one to conclude that windows with the protective air stream remain operative (probing radiation of the atomic absorption spectrometer continues to pass through the central part of radiation transparent windows) after 14 days. The windows without the protective air stream reach a non-operational state after about 8 hours of operation.

Example 3

Determination of Mercury Content in Combustion Gases

Combustion gases have rather complex composition that may include: smoke particles, water vapors, $O_2$, $CO_2$, NO, $NO_2$, $SO_2$, HCl, HF, Hg and its compounds. In addition, the temperature of gas at the sampling point may be about 100-200° C. The sampling probe is connected with the pumping unit which is a heated injecting pump with gas lines. An exemplary embodiment uses a diaphragm pump with Teflon coating of all elements contacting with gas stream as the injecting pump.

Of course these embodiments are exemplary and alterations thereto are possible by those having skill in the relevant technology. Specifically but without limitation, the principles described may be used for determining concentrations of other materials in samples.

Thus the example embodiments and arrangements achieve improved capabilities, eliminate difficulties encountered in the use of prior methods and systems, and attain the desirable results described herein.

In the foregoing description, certain terms have been used for brevity, clarity and understanding. However, no unnecessary limitations are to be implied therefrom because such terms are used for descriptive purposes and are intended to be broadly construed.

Moreover the descriptions and illustrations herein are by way of examples and the invention is not limited to the features shown and described.

Further, it should be understood that features and/or relationships associated with one embodiment can be combined with features and/or relationships from other embodiments. That is, various features and/or relationships from various embodiments can be combined in further embodiments. The inventive scope of the disclosure is not limited to only the embodiments shown or described herein.

Having described the features, discoveries and principles of the exemplary embodiments, the manner in which they are constructed, operated, utilized and carried out, and the advantages and useful results attained, the new and useful arrangements, combinations, methodologies, structures, devices, elements, combinations, operations, processes and relationships are set forth in the appended claims.

We claim:

1. Apparatus comprising:

an analytical cell configured for use in conjunction with an atomic absorption spectrometer usable to determine a mercury concentration in a sample material, wherein the analytical cell includes a body, wherein the body generally bounds an interior area, is elongated along a longitudinal direction and includes a first end and a second end opposed of the first end, a first window adjacent the first end and a second window adjacent the second end, wherein the first and second windows are generally transparent to resonant radiation of mercury, wherein one of the first and second windows is configured to be optically connected with an atomic absorption spectrometer, a gas sample inlet port on the body and longitudinally intermediate of the first and second windows, wherein the gas sample inlet port is configured to deliver into the interior area heated sample material vapor, a pair of gas outlet ports each of which gas outlet ports is configured to enable gas to leave the interior area, wherein a first gas outlet port is positioned longitudinally intermediate of the gas inlet port and the first window, and a second gas outlet port is positioned longitudinally intermediate of the gas inlet port and the second window, a pair of clean gas inlet flow ports, wherein each gas inlet flow port is configured to deliver into the interior area, sample material-free gas, wherein a first clean gas inlet port is positioned to deliver sample material-free gas longitudinally intermediate of the first window and the first gas outlet port, and a second clean gas inlet port is positioned to deliver sample material-free gas longitudinally intermediate of the second gas outlet port and the second window, wherein in operation of the analytical cell, the sample material-free gas flow reduces sample material reaching the first and second windows to maintain window transparency such that heated sample material vapor within the analytical cell can be analyzed through operation of the atomic absorption spectrometer directing radiation through the first and second windows.

2. The apparatus according to claim 1 wherein the analytical cell includes cell heaters.

3. The apparatus according to claim 2 wherein the cell heaters are configured to maintain the interior area at 600-700° C.

4. The apparatus according to claim 2 wherein the other of the first and second windows is operatively connected with a retroreflector.

5. The apparatus according to claim 4 and further comprising:
a thermal atomizer, wherein the thermal atomizer is in hermetic fluid sealed connection with the gas sample inlet port.

6. The apparatus according to claim 5 wherein the thermal atomizer heats sample material vapor to 600° to 950° C.

7. The apparatus according to claim 5 and further comprising:
a sample input unit, wherein the sample input unit is in hermetically sealed fluid connection with the thermal atomizer,
wherein the sample input unit includes a nebulizer in operative connection with a supply of liquid sample material.

8. The apparatus according to claim 5 and further comprising:
a sample injecting pump, wherein the injecting pump is in fluid communication with the thermal atomizer.

9. The apparatus according to claim 7 wherein the nebulizer includes a nozzle, and wherein the thermal atomizer includes an axial elongated interior area, wherein the nozzle is configured to deliver an aerosol spray of sample material coaxially aligned into the axial elongated interior area.

10. The apparatus according to claim 7 and further comprising:
a mixer, wherein the mixer has three ports,
wherein the nebulizer includes a gas port and wherein a first port of the mixer is in operative connection with the nebulizer gas port,
wherein a second port of the mixer is fluidly connected to a distilled water supply, wherein a third port of the mixer is fluidly connected to a supply of carrier gas.

11. The apparatus according to claim 7 wherein the sample input unit contains a holder of the nebulizer, wherein a cavity extends between an interior wall of the holder and the nebulizer,
wherein the cavity is fluidly connected with an internal cavity of the thermal atomizer, and
wherein the cavity of the nebulizer is fluidly connected with a supply of carrier gas.

12. The apparatus according to claim 7 and further comprising:
a gas collector in operative connection with the first and second gas outlet ports, wherein the gas collector includes a cooler and a liquid gas separator.

13. The apparatus according to claim 12 wherein the gas collector further includes a liquid holding reservoir in fluid connection with the liquid gas separator, and a return pump in fluid connection with the liquid holding reservoir.

14. The apparatus according to claim 13 wherein the clean gas inlet flow ports comprise openings through which sample vapor free air is enabled to enter the interior area.

15. The apparatus according to claim 1 wherein each of the pair of clean gas inlet flow ports includes an opening through which sample vapor free air is enabled to enter the interior area.

16. The apparatus according to claim 1 wherein the analytical cell is operatively coupled through the first window with an atomic absorption spectrometer and wherein the second window is optionally coupled with a retroreflector,
wherein the retroreflector is positioned so that radiation from the atomic absorption spectrometer passes through the first and second windows and is returned by the retroreflector through the second window and the first window back to the atomic absorption spectrometer.

* * * * *